United States Patent [19]

Fabinski et al.

[11] 4,180,732

[45] Dec. 25, 1979

[54] NONDISPERSIVE INFRARED GAS ANALYZER

[75] Inventors: Walter Fabinski, Hattersheim; Udo Deptolla, Ober-Olm, both of Fed. Rep. of Germany

[73] Assignee: Hartmann & Braun Aktiengesellschaft, Frankfurt am Main, Fed. Rep. of Germany

[21] Appl. No.: 953,639

[22] Filed: Oct. 23, 1978

[30] Foreign Application Priority Data

Oct. 27, 1977 [DE] Fed. Rep. of Germany ....... 2748089

[51] Int. Cl.² .............................................. G01J 1/00
[52] U.S. Cl. .................................... 250/344; 250/345
[58] Field of Search .................... 250/344, 343, 345

[56] References Cited

U.S. PATENT DOCUMENTS

| 3,725,702 | 4/1973 | Schaefer | 250/343 |
| 3,925,667 | 12/1975 | Staab | 250/344 |

FOREIGN PATENT DOCUMENTS 2811287  9/1978  Fed. Rep. of Germany .......... 250/345

*Primary Examiner*—Alfred E. Smith
*Assistant Examiner*—Carolyn E. Fields
*Attorney, Agent, or Firm*—Smyth, Pavitt, Siegemund, Jones & Martella

[57] ABSTRACT

The sensitivity and selectivity of a two beam analyzer operating with negative filtering and differential absorption-pressure detection is improved by employing differently long cells for the sample gas in the two beam paths, which reduces the effect resulting from overlapping absorption bands of the wanted and of unwanted components in the sample gas.

6 Claims, 2 Drawing Figures

NONDISPERSIVE INFRARED GAS ANALYZER

BACKGROUND OF THE INVENTION

The present invention relates to a nondispersive infrared gas analyzer.

The U.S. Letters Pat. No. 3,925,667 describes a gas analyzer having two infrared beams whose intensity is periodically modulated (interrupted) by a revolving chopper, and the two modulated beams each pass through similar cells containing the sample gas to be analyzed. One of the beams emerging from the respective cell is passed to a single absorption detector chamber, the other beam passes serially through two absorption chambers. All these absorption chambers pertain to a pneumatic detector and the end-absorption chambers are connected to opposite sides of another chamber which is biparted by a membrane whose deflection on account of pressure differences is electrically monitored. The third absorption chamber connects to the same pressure side on the membrane its serial companion is connected to, but through a flow impedence to offset long term pressure differentials between them.

The infrared gas analyzer of that patent operates on the basis of what can be described the principle of negative filtering. This principle is of advantage over so-called positive filtering, if the sample gas contains a component which has an absorption band that overlaps the band of the component to be detected. The cross-sensitivity is simply more pronounced in positive filtering which produces errors accordingly. These aspects have been more fully described generally by Werner Schaefer in "Gasanalyse mit dem Uras bei kompliziert zusammengesetzten Messgasen", from Chemie-Ing.-Techn., 33. Year, 1961/No. 6.

DESCRIPTION OF THE INVENTION

It is an object of the present invention to improve nondispersive gas analysis operating on the basis of negative filtering, i.e. the sample gas is passed through by two intensity modulated radiation beams, the improvement is to relate particularly to sensitivity and selectivity of response.

It is a specific object of the present invention to provide a new and improved nondispersive gas analyzer in which two modulated infrared beams pass separately through sample gas and terminate in separate absorption chambers, containing the gas component to be detected and being connected to a pressure sensitive detector responding to differential pressure of the two chambers and whose output is an electrical signal indicating the content of the concentration of the component to be detected in the sample gas.

In accordance with the preferred embodiment of the invention, it is suggested to provide the path lengths of the two beams through the sample gas differently long; the respective cells differing in length accordingly in that preferably the length of one is about one-half to three-quarter the length of the other. It was found that the sensitivity of the device is greatly increased in this case as will be shown below in a particular example.

DESCRIPTION OF THE DRAWINGS

While the specification concludes with claims particularly pointing out and distinctly claiming the subject matter which is regarded as the invention, it is believed that the invention, the objects and features of the invention and further objects, features and advantages thereof will be better understood from the following description taken in connection with the accompanying drawings in which:

Figure 1:
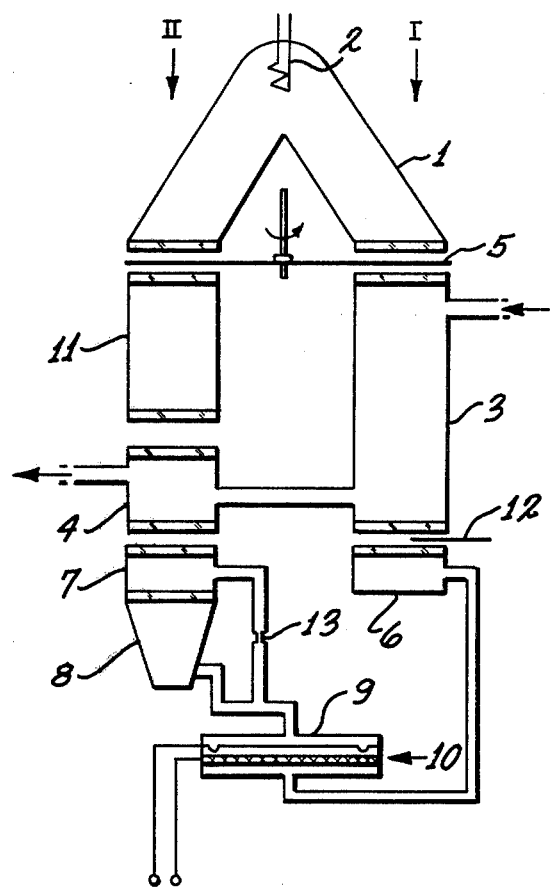
FIG. 1 illustrates somewhat schematically a nondispersive infrared gas analyzer in accordance with the preferred embodiment of the invention.

Proceeding to the detailed description of the drawing, the system and apparatus illustrated includes a source 2 for infrared radiation contained in a beam divider 1 through which two beams are issued along paths denoted generally by I and II. The divider 1 has two exit windows in front of which rotates a chopper 5 which intercepts the two beams in phase synchronism.

The intensity modulated beam of path I passes through a relatively long cell 3 being flown through by sample gas. That sample gas continuous into a smaller sample cell 4 located in the second path II, and downstream from a cell 11 containing a gas which does not absorb infrared radiation. This cell is provided only for reasons of symmetry in geometric path length.

The beam in path I when emerging from cell 3 enters a cell 6 which contains the gas component to be detected. A pair of serially arranged cells 7 and 8 are likewise filled with the gas to be detected and receive the beam in path II after emerging from cell 4. The chamber 8 is of somewhat conical configuration and the two chambers 7 and 8 are interconnected by a high impedance path 13 for long term pressure equalization (see also U.S. Pat. No. 3,952,667, supra).

The two chambers 7 and 8 as so joined (but downstream from the throttle 13) are connected to one side of a pressure differential chamber 9 containing a membrane or diaphragm 10 which biparts the chamber 9 and serves as one capacitive electrode. The second electrode making up this capacitor, is contained in the other portion of the chamber 9 but does not interfer with gas flow. This other side of chamber 9 is connected to cell 6. Thus, the capacitor monitors the pressure differential across the chamber and generates an electrical signal representative thereof. The pressure differential as represented by the electrical signal, is indicative of the concentration of the gas to be detected in the sample gas as flowing through cells 3 and 4.

The beam path I, downstream from cell 3, includes additionally an optical diaphragm 12 to obtain zero calibration in the electrical circuit of the analyzer when the sample gas is free from the gas to be detected. The chambers 6, 7 and 8, and also chamber 9, are preferably contained in a common housing to serve as a construction unit.

The inventive device produces a selectivity increase for the analyzer, over the selectivity in the above identified patent, which will best be explained in an example. It may be assumed that the sample gas is diluted automobile exhaust gas and the component to be detected is CO. The gas, however, containes also $CO_2$ and $H_2O$, which have some overlapping bands with CO in the infrared region. If the cells being passed through by the exhaust fumes were equally long (as is the case in the device of the patent above), a $CO_2$ content from 0 to 3% simulates a CO content of about 0 to 10 ppm CO in a range from 0 to 5 ppm CO to be detected in the fumes. If, as per the device described above, the cell 4 has only ⅔ the length of cell 3, a $CO_2$ content of about 3% simulates a CO content of about 1 ppm. Thus, the selectivity is, in fact, increased tenfold.

Figure 2:
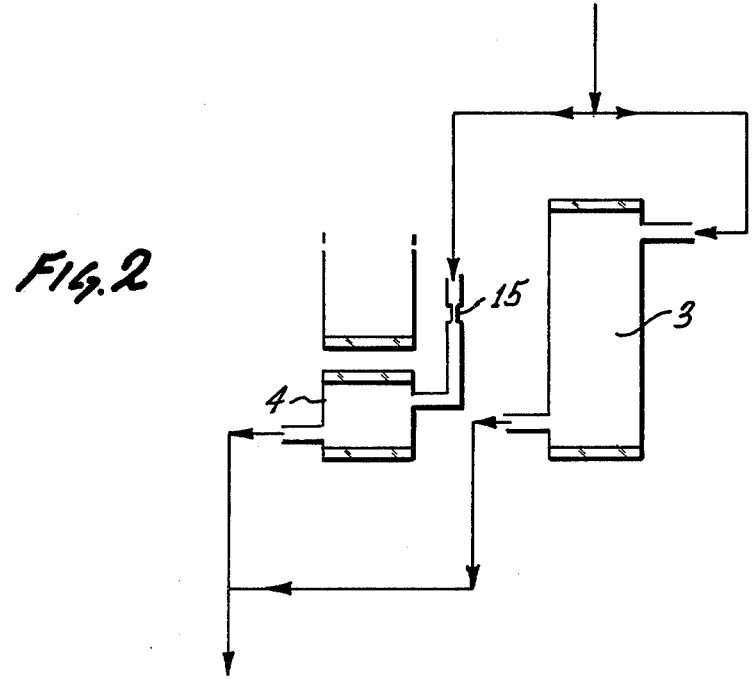
FIG. 2 shows a modification that can be incorporated in the device of FIG. 1.

The device described can be modified as shown in FIG. 2. The cells 3 and 4 are passed through by the sample gas in parallel. In this case, one should place a flow impedance such as a duct constriction 15 into the path to or from the shorter cell, i.e. 4. This flow impedance 15 will be selected so that the time of filling both cells is the same. Similar fill time will be important in the case of changes in the CO content (or of any other gas to be detected) because different fill times for the cells may have an interfering effect in the accuracy.

The invention is not limited to the embodiments described above but all changes and modifications thereof not constituting departures from the spirit and scope of the invention are intended to be included.

We claim:

1. A two beam infrared gas analyzer having means for providing two radiation beams which are periodically intercepted for intensity modulation; further having pressure differential sensing means connected to two absorption chamber means and including a capacitor responsive to a differential chamber as between the two absorption chamber means to provide an electrical signal representing a difference in absorption by the two chamber means, there being an additional absorption chamber filled with the same kind of sample gas to be detected and being disposed in the path of one of the beams, the improvement comprising:

a first cell being passed through by the gas to be analyzed and disposed in the path of the other one of the two radiation beams as modulated but optically in front of one of the two absorption chamber means; and a second cell also being passed through by gas to be analyzed, and being shorter than the first cell in direction of beam propagation and being disposed in the path of the one beam in front of the other absorption chamber means.

2. The improvement as in claim 1, said second cell being about one-half to three-quarter as long as the first cell.

3. The improvement as in claim 1, and including a third cell filled with neutral non-absorbing gas disposed optically in series with the second cell.

4. The improvement as in claim 1, said first and second cells being fluid conductively interconnected in series for sequential passage of the sample gas.

5. The improvement as in claim 1, the first and second cells being passed through by sample gas in parallel, there being a flow path restriction interposed upstream of the second cell.

6. The improvement as in claim 1, wherein the absorption chambers and the pressure differential sensing means constitute a structural unit.

* * * * *